United States Patent [19]

Edwards et al.

[11] Patent Number: 6,077,480
[45] Date of Patent: Jun. 20, 2000

[54] MULTIPLE FLASHPOINT VAPORIZATION SYSTEM

[75] Inventors: Steven J. Edwards, Madison, Ohio; Stephen G. Geist, Raleigh; Paul A. Steen, Apex, both of N.C.

[73] Assignee: Steris Corporation, Mentor, Ohio

[21] Appl. No.: 08/878,539

[22] Filed: Jun. 19, 1997

[51] Int. Cl.[7] ................................ A61L 2/20; A61L 2/24
[52] U.S. Cl. .................. 422/28; 422/29; 422/3; 422/105; 422/108; 422/110; 422/119; 422/292; 422/305; 422/298
[58] Field of Search .............................. 422/27, 306, 28, 422/305, 3, 29, 105, 108, 110, 119, 292, 298

[56] References Cited

U.S. PATENT DOCUMENTS

| | | | |
|---|---|---|---|
| Re. 33,007 | 8/1989 | Bier | 203/12 |
| 3,861,875 | 1/1975 | Joslyn | 23/230 B |
| 4,169,123 | 9/1979 | Moore et al. | 422/29 |
| 4,169,124 | 9/1979 | Forstrom et al. | 422/33 |
| 4,688,585 | 8/1987 | Vetter | 134/56 R |
| 4,909,999 | 3/1990 | Cummings et al. | 422/298 |
| 4,956,145 | 9/1990 | Cummings et al. | 422/28 |
| 5,173,258 | 12/1992 | Childers | 422/27 |
| 5,445,792 | 8/1995 | Rickloff et al. | 422/28 |
| 5,851,485 | 12/1998 | Lin et al. | 422/28 |

FOREIGN PATENT DOCUMENTS

| | | |
|---|---|---|
| 197 174 A1 | of 0000 | European Pat. Off. . |
| 774 263 A1 | of 0000 | European Pat. Off. . |
| WO 90/07366 | of 0000 | WIPO . |
| WO 91/05573 | of 0000 | WIPO . |
| WO 97/04816 | of 0000 | WIPO . |

Primary Examiner—Elizabeth McKane
Assistant Examiner—Fariborz Moazzam
Attorney, Agent, or Firm—Fay, Sharpe, Fagan, Minnich & McKee, LLP

[57] ABSTRACT

A multiple flashpoint vaporization system rapidly sterilizes large enclosures. A plurality of vaporizers (10) inject hydrogen peroxide vapor into streams of carrier gas supplied by a generator (20). Supply lines (30) transport the mixture of carrier gas and hydrogen peroxide vapor to a plurality of regions of an enclosure (32). Monitors (52) monitor hydrogen peroxide vapor concentration or other conditions in each region of the enclosure. A control system (50) adjusts the hydrogen peroxide vapor supply rate in response to the corresponding monitored conditions.

12 Claims, 1 Drawing Sheet

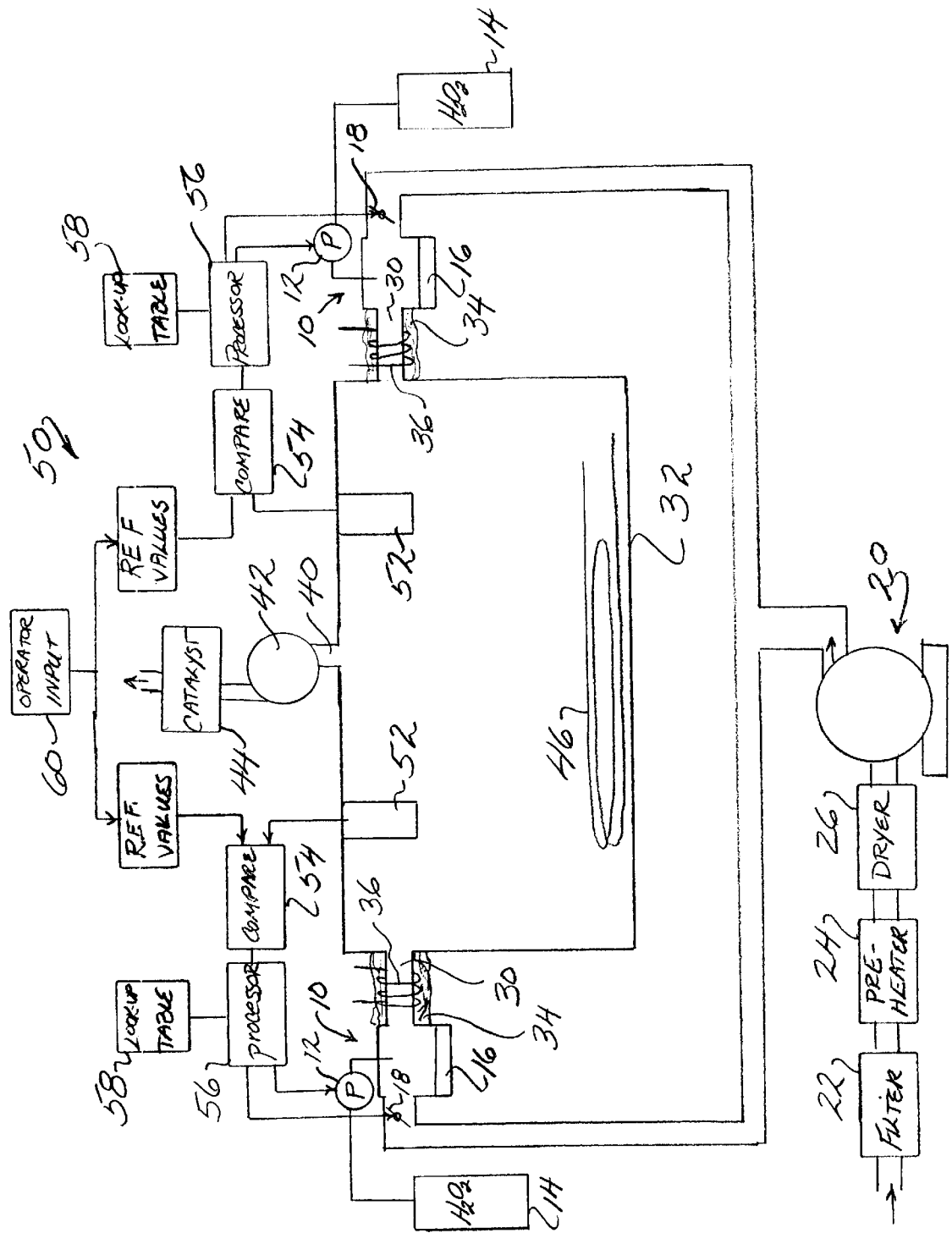

1

MULTIPLE FLASHPOINT VAPORIZATION SYSTEM

BACKGROUND OF THE INVENTION

The present invention relates to the sterilization arts. It finds particular application in conjunction with hydrogen peroxide vaporization systems used in connection with the sterilization of large enclosures, and their contents, and will be described with particular reference thereto. It should be appreciated, however, that the invention is also applicable to other chemical vaporization systems such as peracetic acid vaporization systems.

Sterile enclosures are used by hospitals and laboratories for conducting tests in a microorganism-free environment. Processing equipment for pharmaceuticals and food, and freeze driers also include large enclosures which require sterilizing. Vaporized hydrogen peroxide is a particularly useful sterilant for these purposes because it is effective at low temperatures. Keeping the temperature of the enclosure near room temperature eliminates the potential for thermal degradation of associated equipment and items to be sterilized within the enclosure. In addition, hydrogen peroxide readily decomposes to water and oxygen, which, of course, are not harmful to the operator.

For effective sterilization, the hydrogen peroxide is maintained in the vapor state. Sterilization efficiency is significantly reduced by condensation. Many current hydrogen peroxide sterilizers inject a spray of hydrogen peroxide into a vacuum. The premier systems incorporate a single heated hydrogen peroxide vaporizer. A solution of about 35% hydrogen peroxide in water is injected into the vaporizer which heats it to form a vapor, without breaking it down to water and oxygen. A flow of air carries the vapor to the enclosure.

As the size of the enclosure increases, the demand for hydrogen peroxide is increased and the efficiency of the vaporization system becomes more significant. The capacity of the vaporizer is limited in a number of ways. First, the vaporization process creates a pressure drop, reducing the flow of air through the vaporizer. This increases the sterilization time and effectively limits the size of the enclosure to one which is capable of sterilization within an acceptable time period. Second, to maintain sterilization efficiency, the pressure at which the vapor is generated is limited to that at which the hydrogen peroxide is stable in the vapor state.

Further, large enclosures create problems themselves. Temperature differences throughout the chamber require different concentrations of the sterilant to compensate for condensation on cooler surfaces. Items within the enclosure require different concentrations of sterilant for optimum exposure because of their relative absorbencies. Pumping the vapor to more distant regions within the enclosure increases the extent of condensation within the vapor supply lines, reducing effectiveness.

One solution was to increase the size of the vaporizer and the injection rate of hydrogen peroxide into the vaporizer. Although helpful, the larger vaporizer still suffers from concentration variations and condensation concerns.

The present invention provides a new and improved vaporization system which overcomes the above referenced problems and others.

SUMMARY OF THE INVENTION

In accordance with one aspect of the present invention, a hydrogen peroxide vaporization system is provided. A plurality of vaporizers inject vaporized hydrogen peroxide into a stream of carrier gas. A generator supplies the carrier gas to the vaporizers. A supply line, or lines, transports the mixture of carrier gas and vaporized hydrogen peroxide from the vaporizers to an enclosure for sterilization of the enclosure and its contents.

In accordance with another aspect of the present invention, a method of supplying vaporized hydrogen peroxide to an enclosure is provided. A solution of hydrogen peroxide is vaporized by a plurality of vaporizers. The vapor is mixed with a flow of a carrier gas and transported by supply lines to the enclosure.

One advantage of the present invention is that optimum sterilization throughout a large enclosure is achieved.

Another advantage is that sterilization is effected in a short period of time.

Another advantage of the present invention is that the air flow and hydrogen peroxide injection rates can be increased.

Another advantage resides in improved hydrogen peroxide concentration uniformity.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

The FIGURE is a cross section of a preferred embodiment of a hydrogen peroxide vaporization system in accordance with the present invention.

DETAILED DESCRIPTION OF THE PREFERRED EMBODIMENTS

With reference to the FIGURE, a plurality of vaporizers 10 inject vaporized hydrogen peroxide into a carrier gas. More specifically, hydrogen peroxide is pumped, preferably by an adjustable metering pump 12 from a cartridge or reservoir 14 and injected at a measured rate in droplets or mist form onto a heated plate 16. The hydrogen peroxide vaporizes on contact with the plate and is entrained in a flow of the carrier gas. The temperature of the plate is maintained at a temperature below that at which dissociation of the hydrogen peroxide occurs. A carrier gas flow regulator or baffle 18 adjustably controls the flow of carrier gas. Adjusting the metering pump 12 and the carrier gas flow regulator 18 controls the rate at which the hydrogen peroxide vapor is produced.

The carrier gas is preferably air, although other gases which are unreactive toward hydrogen peroxide are also contemplated. A carrier gas generator 20, such as a pump or container of pressurized gas, supplies the carrier gas to the vaporizers 10. When atmosphere air is the carrier gas, filters 22 remove contaminants. Preferably, a preheater 24 raises the temperature of the carrier gas before it reaches the vaporizers 10, reducing condensation in the supply lines and raising the saturation concentration of hydrogen peroxide vapor. Optionally, a dryer 26 or the like controls the humidity of the carrier gas.

Supply lines 30 transport the mixture of carrier gas and vaporized hydrogen peroxide from the vaporizers 10 to an enclosure 32. To reduce the risk of condensation, the length of the supply lines 30 is minimized. To reduce the risk of condensation further, insulation 34 and/or heaters 36 surround the supply lines 30. Optionally, two or more supply lines connect each vaporizer to two or more regions of the enclosure 32.

A vent 40 permits controlled release of excess pressure in the enclosure. Optionally, vacuum pump 42 evacuates the enclosure prior to hydrogen peroxide vapor introduction. Evacuation increases the rate at which hydrogen peroxide vapor can be drawn into the chamber, reducing the supply pressure of the hydrogen peroxide vapor and thereby avoiding condensation. A catalyst 44 or the like breaks down any residual hydrogen peroxide in the venter gas. optionally, a heater 46 raises the temperature of and within the enclosure 32 prior to, and during, sterilization. Raising the temperature in the enclosure or at least its surfaces also reduces vapor condensation.

Sterilizable enclosures include microorganism-free work areas, freeze dryers, and pharmaceutical or food processing equipment. Whether high sterilization temperatures and or evacuation of the enclosure during sterilization are feasible depends on the construction of the enclosure and the nature of its contents. For example, sterilizable work areas are typically constructed of non-rigid plastic materials which do not withstand high temperatures and low pressures. Food processing equipment, in contrast, is often required to withstand high temperatures and pressures during processing operations and is more easily adapted to achieving more optimal sterilization conditions through evacuation and heating.

Preferably the hydrogen peroxide concentration is 30–35% by weight aqueous hydrogen peroxide. At this level, condensation of hydrogen peroxide is limited, while sterilization in a short period of time is achieved.

The hydrogen peroxide vapor is held in the enclosure 32 until sterilization is complete. Optionally, the vacuum pump 42 draws out the hydrogen peroxide vapor from the enclosure following sterilization. This reduces the time required for dissipation of the hydrogen peroxide, and returns the enclosure to useful activity more quickly.

In the illustrated embodiment, the vaporizers are located at a distance from the carrier gas generator, in close proximity to the enclosure. The rate of introduction of hydrogen peroxide by the individual vaporizers is adjustable so as to optimize hydrogen peroxide vapor distribution within the enclosure.

Differences in temperature and absorbency of materials within the chamber, flow patterns in the chamber, and chamber shape are among the factors influencing the optimum rate of introduction. Preferably a control system 50 regulates the introduction of hydrogen peroxide to the vaporizers in accordance with local conditions within the chamber. A plurality of monitors 52 monitor conditions within the enclosure 32. The monitors include temperature sensors, humidity or vapor concentration sensors, air flow or turbulence sensors, pressure sensors, and the like. The control system includes a comparator 54 for comparing the monitored condition signals from the monitors with preselected ideal hydrogen peroxide vapor concentration and other conditions as indicated by reference signals. Preferably, the comparator determines a deviation of each monitored condition signal from the corresponding reference signal or a reference value. Preferably, a plurality of the conditions are sensed and multiple comparitors are provided. A processor 56 addresses a pre-programmed look up table 58 with each deviation signal (or combination of deviations of different conditions) to retrieve a corresponding adjustment for each vaporizer. Other circuits for converting larger deviations to larger adjustments and smaller deviations to smaller adjustments are also contemplated. Alternately, the error calculation can be made at very short intervals with constant magnitude increases or decreases when the monitored condition is below or above the reference points.

The adjustment values from the look up table adjust the hydrogen peroxide metering pump 12 and the carrier gas regulator 18 to bring the monitored conditions to the reference values. For example, vapor injection rates are increased by vaporizers near regions with lower vapor concentration, lower temperatures, higher pressure, and the like. Vapor production rates are reduced in response to higher sensed vapor concentration, higher sensed temperatures, lower pressure, and the like. The processor, optionally, also controls the chamber heater 46, circulation fans in the enclosure, the vacuum pump 42, or the like. Optionally, an operator input 60 enables the operator to adjust the reference signal in each region to cause higher or lower concentrations in selected regions.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A hydrogen peroxide sterilization system comprising:
    (a) a plurality of vaporizers which independently inject vaporized hydrogen peroxide into a carrier gas at differently adjustable rates, each vaporizer including a separate liquid hydrogen peroxide regulator for simultaneously, variably, and independently controlling a rate of injection of hydrogen peroxide into the vaporizer;
    (b) a carrier gas supply for supplying a flow of the carrier gas to the vaporizers;
    (c) at least one supply line for transporting the hydrogen peroxide vapor and the carrier gas from each vaporizer to different regions of an enclosure to be sterilized; and
    a control system for controlling each of the vaporizers to adjust independently the rate at which each vaporizer injects vaporized hydrogen peroxide into the carrier gas so as to provide each of the regions with a selected concentration of hydrogen peroxide vapor.

2. The system as set forth in claim 1, wherein each vaporizer further includes a carrier gas flow regulator for separately controlling a flow rate of carrier gas to the vaporizer to regulate a rate of hydrogen peroxide vapor production.

3. A hydrogen peroxide sterilization system comprising:
    (a) a plurality of vaporizers, each of the vaporizers independently injecting vaporized hydrogen peroxide into a carrier gas at an independently regulated variable rate;
    (b) a carrier gas generator for supplying a flow of the carrier gas to the vaporizers; and,
    (c) at least one supply line for each vaporizer for transporting the hydrogen peroxide vapor and the carrier gas from each vaporizer to different regions of an enclosure to be sterilized, each of the vaporizers supplying hydrogen peroxide vapor to a different region of the enclosure;

(d) a plurality of monitors for detecting conditions in each of the different regions of the enclosure; and (e) a control system for controlling each of the vaporizers to adjust independently the rate at which each vaporizer injects vaporized hydrogen peroxide into the carrier gas in accordance with the detected conditions in the different regions.

4. A hydrogen peroxide sterilization system comprising:

(a) a plurality of vaporizers for injecting hydrogen peroxide vapor into a carrier gas;

(b) a carrier gas generator for supplying a flow of carrier gas to the vaporizers;

(c) at least one supply line for transporting the hydrogen peroxide vapor and the carrier gas from each vaporizer to different regions of an enclosure to be sterilized, each of the vaporizers supplying hydrogen peroxide vapor to at least one of the different regions of the enclosure;

d) a plurality of monitors for detecting conditions in each of the different regions of the enclosure; and, e) a control system for independently regulating a rate at which hydrogen peroxide vapor is supplied by each vaporizer in accordance with the detected conditions in each region of the enclosure.

5. The system as set forth in claim 4, wherein the control system includes a comparator for comparing the enclosure condition signals from the monitors with reference values to determine a deviation therebetween.

6. The system as set forth in claim 5, wherein the control system further includes a processor for addressing a preprogrammed look-up table in accordance with the deviations determined by the comparator and retrieving vaporizer adjustments values therefrom.

7. The system as set forth in claim 6, wherein the vaporizer adjustment values include a liquid hydrogen peroxide adjustment value and a carrier gas adjustment value and wherein each vaporizer includes:

a liquid hydrogen peroxide regulator for regulating a supply rate of liquid hydrogen peroxide to the vaporizer, the processor controlling the liquid hydrogen peroxide regulator in accordance with the hydrogen peroxide adjustment value retrieved from the look-up table; and, a carrier gas regulator for regulating a supply rate of the carrier gas to the vaporizer, the processor controlling the liquid hydrogen peroxide regulator in accordance with the carrier gas adjustment value from the look-up table.

8. A method for supplying vaporized hydrogen peroxide to an enclosure comprising:

at a first site, vaporizing a liquid solution of hydrogen peroxide to form hydrogen peroxide vapor at a first rate of vaporization;

at a second site, vaporizing a liquid solution of hydrogen peroxide to form hydrogen peroxide vapor at a second rate of vaporization which is independent of the first rate;

providing streams of carrier gas to the first and second sites;

entraining the hydrogen peroxide vapor into the streams of carrier gas at the first and second sites;

independently transporting the hydrogen peroxide vapor and carrier gas from the first and second sites to first and second regions of the enclosure; and, independently regulating the first and second rates of vaporization at the first and second sites and entraining hydrogen peroxide vapor into the streams of carrier gas.

9. The method as set forth in claim 8, further including:

holding the hydrogen peroxide vapor within the enclosure until sterilization is achieved.

10. The method as set forth in claim 8, further including drawing a vacuum within the enclosure prior to sterilization.

11. The method as set forth in claim 8, further including monitoring conditions in the first and second regions of the enclosure.

12. A method for supplying vaporized hydrogen peroxide to an enclosure comprising:

at a first site, vaporizing a liquid solution of hydrogen peroxide to form hydrogen peroxide vapor;

at a second site, vaporizing a liquid solution of hydrogen peroxide to form hydrogen peroxide vapor;

providing streams of carrier gas to the first and second sites;

entraining the hydrogen peroxide vapor into the streams of carrier gas at the first and second sites;

independently transporting the hydrogen peroxide vapor and carrier gas from the first and second sites to first and second regions of the enclosure;

monitoring conditions in the first and second regions of the enclosure;

determining deviations of the monitored conditions in each region from preselected conditions; and, independently regulating (i) a first variable rate at which the liquid hydrogen peroxide solution is vaporized and entrained in the carrier gas at the first site in accordance with the determined deviations in the first region and (ii) a second variable rate at which liquid hydrogen peroxide solution is vaporized and entrained in the carrier gas at the second site in accordance with the determined deviations in the second region.

* * * * *